(12) United States Patent
McCall (10) Patent No.: US 8,398,575 B1
(45) Date of Patent: Mar. 19, 2013

(54) EARLY WARNING AND SHUTDOWN SYSTEM FOR HEMODIALYSIS

(76) Inventor: Kenneth Shawn McCall, Owasso, OK (US)

( * ) Notice: Subject to any disclaimer, the term of this patent is extended or adjusted under 35 U.S.C. 154(b) by 543 days.

(21) Appl. No.: 12/630,376

(22) Filed: Dec. 3, 2009

Related U.S. Application Data (63) Continuation of application No. 12/607,818, filed on Oct. 28, 2009, now Pat. No. 8,235,930, and a continuation of application No. 11/832,274, filed on Aug. 1, 2007, now Pat. No. 7,670,289, and a continuation of application No. 11/306,947, filed on Jan. 17, 2006, now Pat. No. 7,641,612.

(51) Int. Cl.
*A61M 37/00* (2006.01)
*A61B 5/00* (2006.01)

(52) U.S. Cl. .................. 604/4.01; 604/5.01; 600/371

(58) Field of Classification Search ........ 604/4.01–6.16; 210/600, 634, 645–651; 600/362, 371
See application file for complete search history.

(56) References Cited

U.S. PATENT DOCUMENTS

| | | |
|---|---|---|
| 3,399,971 A | 9/1968 | Kita |
| 4,122,838 A | 10/1978 | Leonard |
| 4,239,495 A | 12/1980 | Gindler et al. |
| 4,350,155 A | 9/1982 | Thompson |
| 4,378,808 A | 4/1983 | Lichtenstein |
| 4,602,249 A | 7/1986 | Abbott |
| 4,619,653 A | 10/1986 | Fischell |
| 4,699,615 A | 10/1987 | Fischell et al. |
| 4,717,378 A | 1/1988 | Perrault et al. |
| 4,731,051 A | 3/1988 | Fischell |
| 4,784,645 A | 11/1988 | Fischell |
| 4,787,398 A | 11/1988 | Garcia et al. |
| 5,153,827 A | 10/1992 | Coutre et al. |
| 5,399,445 A | 3/1995 | Tinker |
| 5,468,621 A | 11/1995 | Kojima et al. |
| 5,557,263 A | 9/1996 | Fisher et al. |
| 5,790,036 A | 8/1998 | Fisher et al. |
| 6,057,689 A | 5/2000 | Saadat |
| 6,077,443 A * | 6/2000 | Goldau ..................... 210/741 |
| 6,689,100 B2 | 2/2004 | Connelly et al. |
| 6,752,785 B2 | 6/2004 | Van Antwerp et al. |
| 6,764,465 B2 | 7/2004 | Chen |
| 6,846,303 B2 | 1/2005 | Eakins et al. |
| 6,878,132 B2 | 4/2005 | Kipfer |
| 6,921,383 B2 | 7/2005 | Vitello |
| 6,942,643 B2 | 9/2005 | Eakins et al. |
| 6,979,306 B2 * | 12/2005 | Moll ........................ 604/4.01 |
| 2002/0198483 A1 * | 12/2002 | Wariar et al. ............. 604/5.01 |
| 2005/0010265 A1 | 1/2005 | Fassio et al. |

(Continued)

FOREIGN PATENT DOCUMENTS

WO 9924145 5/1999

OTHER PUBLICATIONS

Discussion of Venous Needle Dislodgement During Hemodialysis: An Unresolved Risk of Catastrophic Hemorrhage:, Dr. Stephen Sandroni (Hemodialysis International, Jan. 2005; 9:102), European Dialysis & Transplant Nurses Association European Renal Care Association; http:/www.edtnaerca.org/pages/education/journalclub/summary2005_2.php.

(Continued)

*Primary Examiner* — Philip R Wiest
(74) *Attorney, Agent, or Firm* — Head, Johnson & Kachigian, P.C.

(57) ABSTRACT

An early warning and shutdown system that connects to a fluid loss detection device for dressings at pre-existing port sites, catheter sites, operative sites, ostomy sites, drain sites, line sites such as those utilized in hemodialysis, wound sites, or other areas for which monitoring of fluid or blood loss is medically indicated. The early warning and shutdown system sounds an alarm when the fluid loss detection device senses a loss of fluid, and then compresses a return tube carrying such fluid to stop further fluid loss if the fluid loss continues.

9 Claims, 10 Drawing Sheets

U.S. PATENT DOCUMENTS

2005/0038325 A1   2/2005   Moll
2007/0293748 A1   12/2007   Engvall et al.

OTHER PUBLICATIONS

"Venous Needle Dislodgement: How to Mnimise the Risks", Jean-Pierre Van Waeleghem et al.; Journal of Renal Care 2008, p. 163-168.

"Recommendations for Preventing Transmission of Infections Among Chronic Hemodialysis Patients", MMWR, Apr. 27, 2001/SO(RROS); 1-43; http://www.cdc.gov/MMWR/preview/mmwrhtml/rr5005a1,htm.

\* cited by examiner

EARLY WARNING AND SHUTDOWN SYSTEM FOR HEMODIALYSIS

CROSS-REFERENCE

This application is a continuation-in-part patent application of U.S. patent application Ser. No. 12/607,818 filed Oct. 28, 2009, which is a continuation-in-part patent application of U.S. patent application Ser. No. 11/832,274 filed Aug. 1, 2007, which is a continuation-in-part patent application of U.S. patent application Ser. No. 11/306,947 filed Jan. 17, 2006, all incorporated in their entireties herein by reference.

STATEMENT REGARDING FEDERALLY SPONSORED RESEARCH OR DEVELOPMENT

Not Applicable.

REFERENCE TO A SEQUENCE LISTING, A TABLE, OR A COMPUTER PROGRAM LISTING COMPACT DISC APPENDIX

Not Applicable.

BACKGROUND OF THE INVENTION

1. Field of the Invention

The present invention relates to an early warning and shutdown system for hemodialysis, and more particularly to a system that provides a warning if a hemodialysis return line access site is leaking and will cause the hemodialysis system to shut down if the leak continues.

2. Prior Art

There are any number of situations in which the loss of blood or fluid from one or more body locations is medically significant. Hemodialysis, for example, is a known medical procedure through which a person's blood is cleansed of toxins. Hemodialysis is often prescribed when the kidneys no longer function properly for any of a number of reasons. Hemodialysis is typically performed at a hospital or dialysis center although there is interest in, and a trend toward, at-home use. In a dialysis treatment, the patient is connected to a hemodialysis machine via two tubes. The first tube is a blood intake tube and is responsible for removing blood from the patient and transferring it to the machine. When the blood enters the machine, it is cleaned via semi-permeable filters and then is pumped back to the patient through a blood return tubing. Before hemodialysis can be done, a doctor must make an entrance, often called an "access", into the patient's blood vessels. This is sometimes done by minor surgery in the leg, arm or neck. The best access for many patients is called a "fistula". Minor surgery may be performed to join an artery to a vein under the skin to make a larger vessel.

The dialysis process can take several hours for each procedure and may be done more than once per week depending on the condition. Even if done in the supervision of medical professionals, a patient cannot be monitored every minute. Additionally, a blanket or blankets will often be placed on the patient and the patient may attempt to nap or sleep during the procedure.

There have been reports of the return line becoming accidentally dislodged or pulled from the access site in the patient. If the dialysis machine and its accompanying pump continue to operate, blood will be drawn from the patient but will not properly be returned to the patient. If this condition continues, the patient can suffer loss of blood and even death. While the hemodialysis machines have existing pressure sensing devices, they may not sense the condition if the blood continues to pump. Additionally, if the patient is sleeping or if medical personnel are not constantly observing the entire procedure, blood loss may occur until it is discovered.

Several prior attempts have been made relating to various leak detection systems. For example, Van Antwerp et al. (U.S. Pat. No. 6,752,785) show a wide variety of leak detection devices including devices as shown in FIGS. 10(*a*), 10(*b*) and 10(*c*). Each of these devices must be applied to the body of a user before a needle is inserted since each includes an enclosed circular opening. The Van Antwerp devices cannot be installed once the return line is attached to the patient. If the Van Antwerp device was placed on the patient first, it would involve breaking the sterile field which is created and normally desirable on the skin of the patient before insertion of the needle. If the Van Antwerp device were to be placed prior to inserting the needle into the patient, the sterile field of the access site would be compromised, possibly resulting in an infection of the patient's blood.

Accordingly, it would be desirable to provide for protection of hemodialysis patients from exsanguination.

It would be desirable to provide a blood and fluid loss detection device which might be installed, and a method for installing the device, around a pre-existing return line or needle connected to the patient, as well as a pre-existing operative site, a catheter or port site, a drain site, an ostomy site, or a wound site.

It would also be desirable to provide a blood loss detection device and method which is simple and modular in design which could be easily placed or replaced without interruption of treatment.

It would further be desirable to provide a blood loss detection device and method having a modular connection with a sensor system to confirm the modular connection.

It would also be desirable to provide a blood loss detection device having a radio transmission means for wireless communication of alarm information.

It would further be desirable to provide an alarm and a shut-down system which operates in conjunction with or separately from existing devices such as hemodialysis systems.

SUMMARY OF THE INVENTION

The present invention provides an early warning and shutdown system for hemodialysis comprising a fluid loss detection device surrounding a return access site through which a return line enters a patient's body and an automatic shutdown device connected to the fluid loss detection device. The fluid loss detection device may comprise an emergency shut-down circuit loop wherein the emergency shut-down circuit loop is activated by a fluid leak.

The automatic shutdown device may comprise a channel capable of receiving the return line and a clamping mechanism located adjacent the channel such that the clamping mechanism does not compress the return line when the clamping mechanism is in an open position but is capable of compressing the return line to stop fluids from flowing therethrough when the clamping mechanism is in an engaged position. The automatic shutdown device automatically moves the clamping mechanism from the open position to the engaged position when the emergency shut-down circuit loop is activated by a fluid leak.

The fluid loss detection device may further comprise an early warning alarm circuit loop wherein said warning alarm circuit loop is activated by a smaller fluid leak than the fluid leak that activates the emergency shut-down circuit loop. The automatic shutdown device may further comprise an alarm wherein the alarm is activated when the warning alarm circuit loop is activated. The alarm may produce sounds, lights, vibrations, or any combination thereof. The automatic shutdown device may further comprises an alarm wherein the alarm is activated when the emergency shut-down circuit loop is activated, and the alarm may produce sounds, lights, vibrations, or any combination thereof.

The fluid loss detection device may connect to the automatic shutdown device via a modular connector. In one embodiment, the clamping mechanism may be spring loaded. Alternatively, the clamping mechanism may be actuated by electrical, mechanical, pneumatic, electromechanical or electropneumatic force. The automatic shutdown device may further comprise a bracket or strap capable of securing the return line within the channel. The automatic shutdown device may attach to the patient's arm.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's shape, construction and the arrangement of its components without departing from the spirit and scope of this disclosure. It is understood that the invention is not limited to the embodiments set forth herein for purposes of exemplification.

The disclosure herein may be applied to a number of situations in which it is medically, diagnostically or clinically advisable to monitor blood and fluid loss. The disclosure herein may be utilized at operative sites, drain sites, port sites, catheter sites, wound sites, ostomy sites, or any other bodily location where blood and fluid loss are to be monitored.

Figure 1:
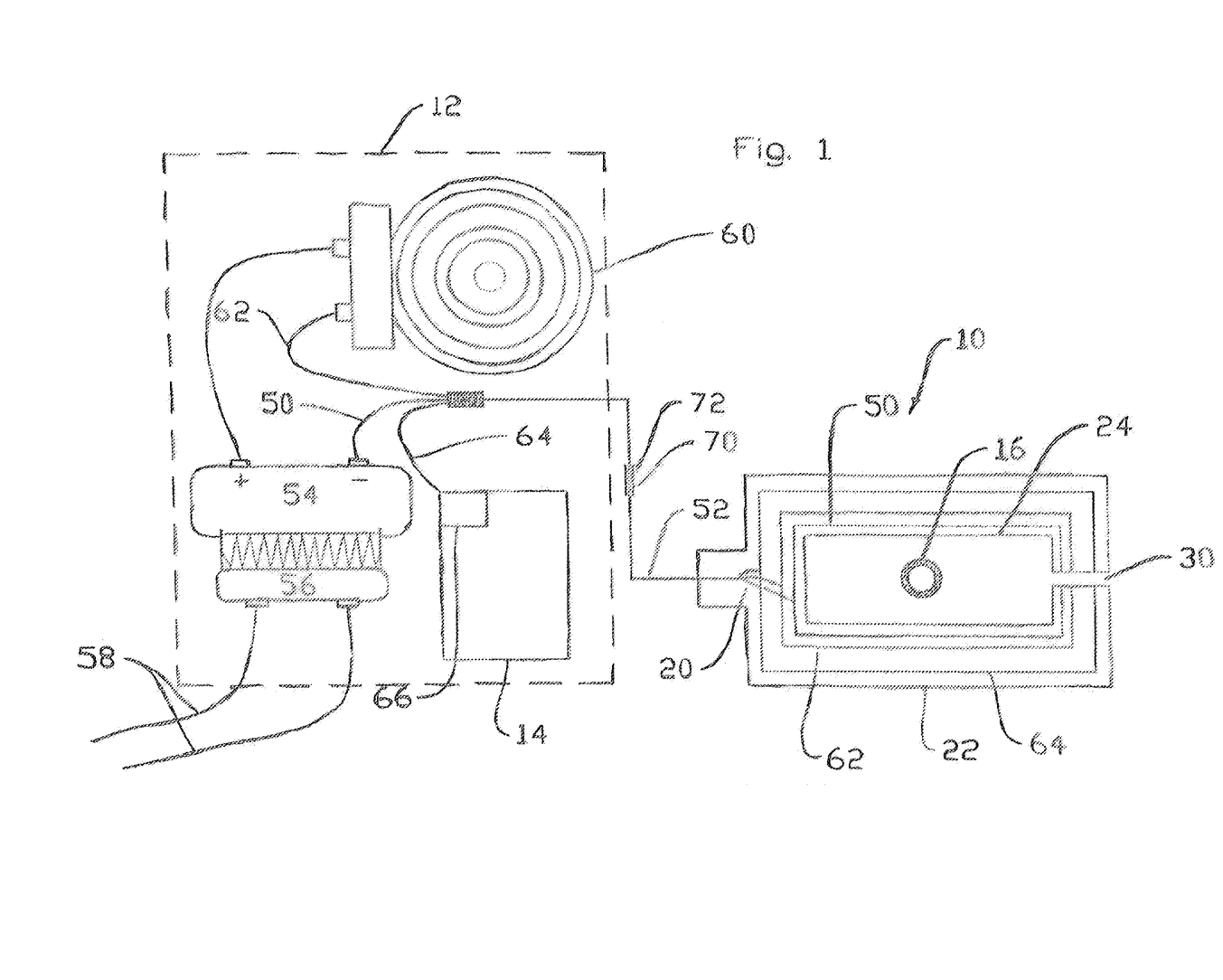
FIG. 1 is a simple diagrammatic view of a blood loss detection device in communication with a hemodialysis system.

Referring to the drawings in detail, FIG. 1 illustrates a simple diagrammatic view of a blood loss detection device 10 constructed in accordance with U.S. patent application Ser. No. 12/607,818 filed Oct. 28, 2009, from which the present application is a continuation-in-part, and which is itself a continuation-in-part patent application of U.S. patent application Ser. No. 11/832,274 filed Aug. 1, 2007, which is a continuation-in-part patent application of U.S. patent application Ser. No. 11/306,947 filed Jan. 17, 2006, all incorporated in their entireties herein by reference.

In one embodiment, the blood loss detection device 10 is utilized with and operates along with a hemodialysis system, represented by dashed lines 12.

Hemodialysis machines and the hemodialysis procedure are both well-known. A patient (not shown) will have a fluid intake tube connected through an access into the blood vessels of the patient. The blood is pumped via a pump (shown diagrammatically by box 14) into and through the hemodialysis machine 12 where the blood is cleansed. The blood is thereafter returned via a blood return line 201 to the patient through a return access site 16.

The detection device 10 includes a patch 20 having a boundary or external edge 22 extending around and circumnavigating the entire patch. The patch 20 and its boundary edge 22 may take many configurations including, as shown in FIG. 1, a substantially rectangular form.

The patch 20 also includes an opening 24 through the patch which forms a target for receipt of the return access site 16 and the return blood line 201 from the hemodialysis machine 12.

A slit 30 through the patch 20 extends from the boundary edge 22 to the patch opening 24. Accordingly, the patch forms an enclosure and surrounds the return access site 16 with the exception of the slit 30. The ends may be overlapped to form a complete enclosure.

The blood access site monitor consists of a base typically with adhesive backing, would be able to substantially encircle the blood access site, and within its inner and outer boundaries contains the primary input circuit and required number of monitoring circuits. The access site monitoring device or patch should be composed of a permeable material that would facilitate transfer of any blood or fluid across the primary input conductors and monitoring circuits.

Figure 2:
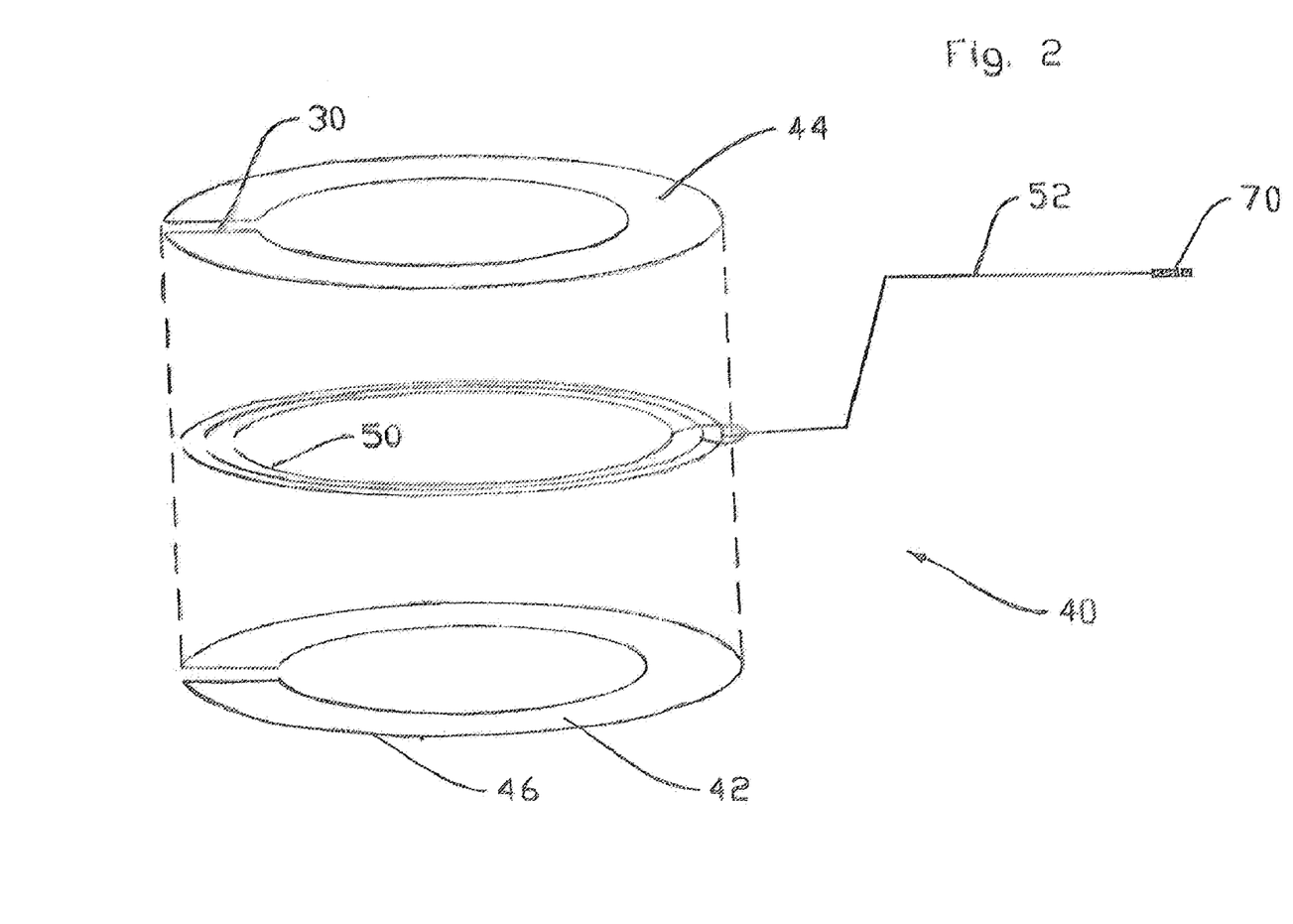
FIG. 2 illustrates an exploded view and FIG. 3 illustrates a top view of an alternate embodiment of the detection device.
Figure 3:
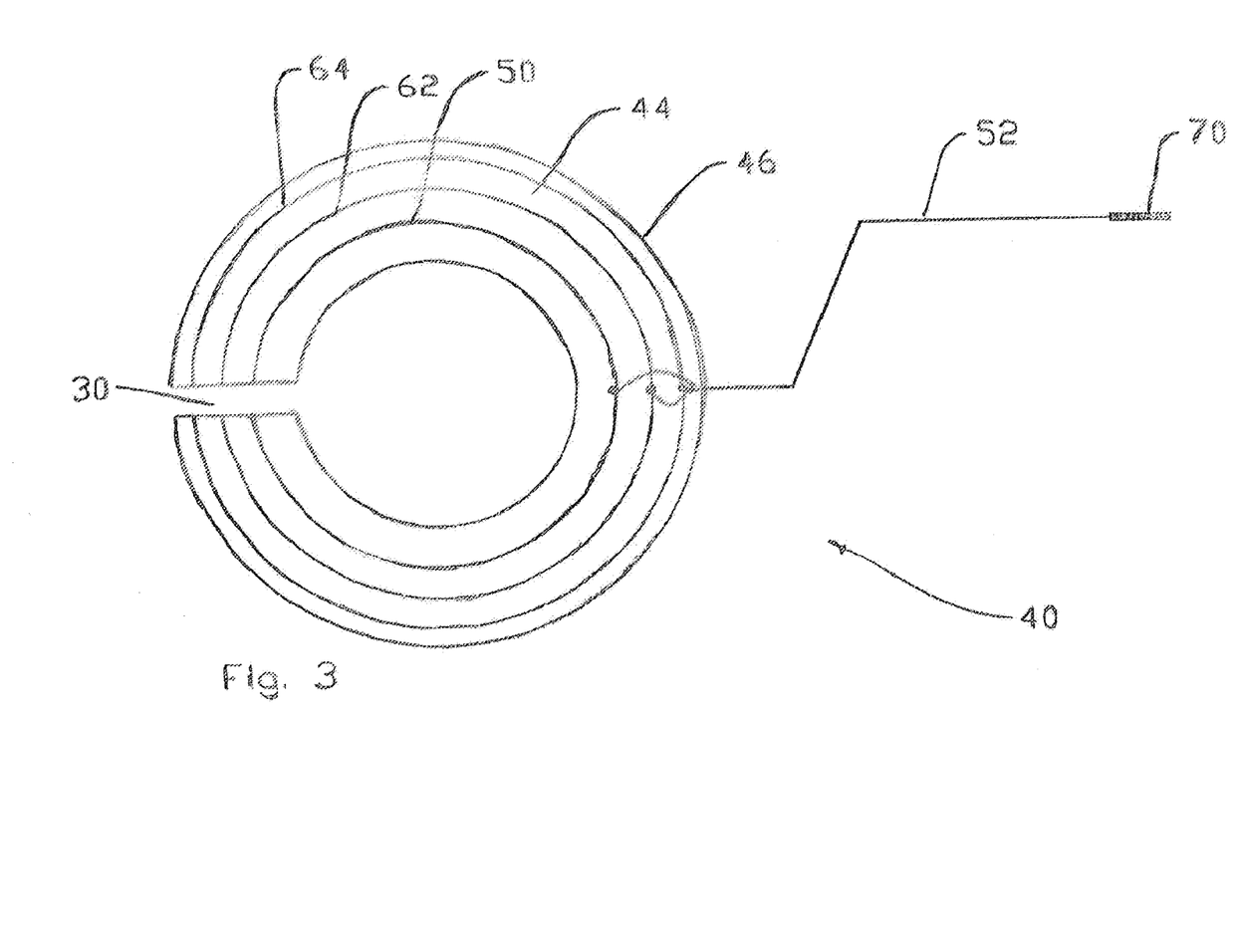

FIGS. 2 and 3 illustrate an alternate embodiment of the detection device 10. FIG. 2 shows an exploded view of an alternate embodiment 40 while FIG. 3 illustrates a top view. The patch 40 includes a first layer 42 having an adhesive base designed to adhere to a skin of a patient. Above the first layer 42 are the electrical conductors to be described. A top layer 44 covers both the electrical conductors and the first layer 42. The boundary edge 46 of the alternate embodiment 40 is in the form of a circle.

Finally, an optional transparent cover (not shown) could be adhesively secured to the top layer 44. The cover might be transparent to allow for visual observation but retain any blood loss.

With reference to FIG. 1 and continuing reference to FIGS. 2 and 3, a primary loop circuit 50 extends through a multi-conductor cable 52 via a primary input loop conductor to the patch (reference numeral 10 in FIG. 1 and reference numeral 40 in FIGS. 2 and 3). The primary input conductor circuit loop 50 may terminate at a pair of opposed ends at the slit 30 in the patch, as shown in FIGS. 1 through 7, or may form a complete loop, as shown in FIG. 8 and described below. The multi-conductor cable 52 carries the primary loop circuit conductor to a DC voltage power supply 54 which, in turn, is connected to transformer 56 and thereafter connected to alternating current power supply 58. The power supply is, in turn, wired to an audio alarm 60. Accordingly, the primary loop input conductor 50 delivers and provides operational voltage to the detection device 10.

An early warning alarm loop circuit 62 passes from the multi-conductor cable 52 into the patch 20. The early warning alarm loop circuit 62 may terminate at two ends at the slit 30, as shown in FIGS. 1 through 7, or may form a complete loop, as shown in FIG. 8 and described below. The early warning alarm loop circuit 62 passes from the patch 20 through the multi-conductor cable 52 and back to the audio alarm 60. An emergency shut-down circuit loop 64 extends from the multi-conductor cable 52 to the patch 20. The emergency shut-down circuit loop 64 may terminate at two ends at the slit 30, as shown in FIGS. 1 through 7, or may form a complete loop, as shown in FIG. 8 and described below. The emergency shut-down circuit 64 may extend through the multi-conductor cable 52 to the dialysis machine 12 and, in particular, to the pump 14. The emergency shut-down circuit may include a switch mechanism 66 to shut down the dialysis machine 12 and, in particular, the pump 14.

As shown in FIG. 8, each of the primary loop circuit 50, the early warning alarm loop circuit 62, and the emergency shut-down circuit loop 64 may form a complete loop originating at an input and ending at an output allowing for a simple continuity check to verify each loop is complete and functioning properly. The primary loop circuit 50 has an input 150 wherein the input voltage may be applied. The input voltage may be verified at output 152. The integrity of the early warning alarm loop circuit 62 may be verified by monitoring the continuity of the complete early warning loop between inputs 154 and 156. The integrity of the emergency shutdown loop would be monitored in the same manner but utilizing inputs 158 and 160.

This arrangement would allow a staged response to any and all loop failures. The response to the failure of either the primary input loop circuit 50 or the emergency shut-down circuit loop 64 may be termination of the treatment due to losing the critical response protocols. The response to the failure of the early warning alarm loop circuit 62 may only necessitate a low level alarm.

The present invention is modular in design so that the blood loss detection device 10 may be quickly installed, removed and replaced as desirable.

Figure 9:
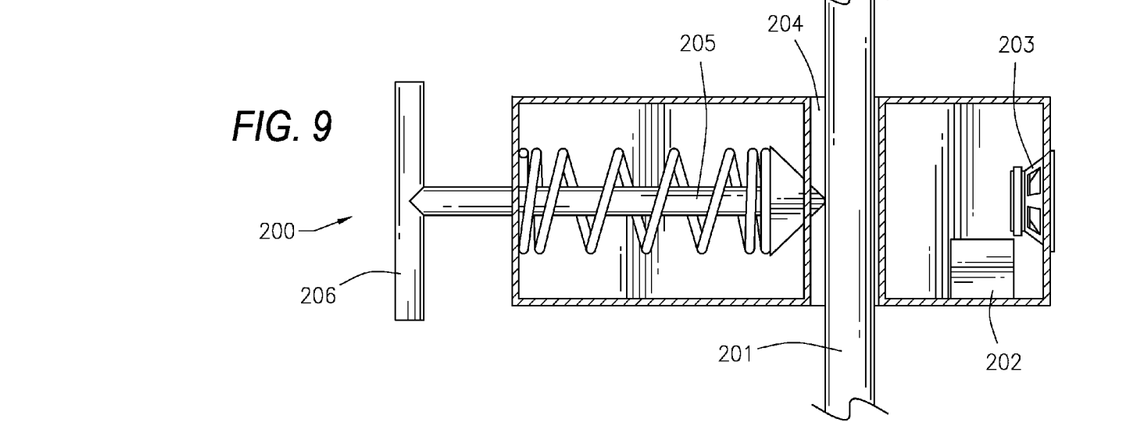
FIG. 9 depicts a top view of an early warning and shutdown device.
Figure 10:
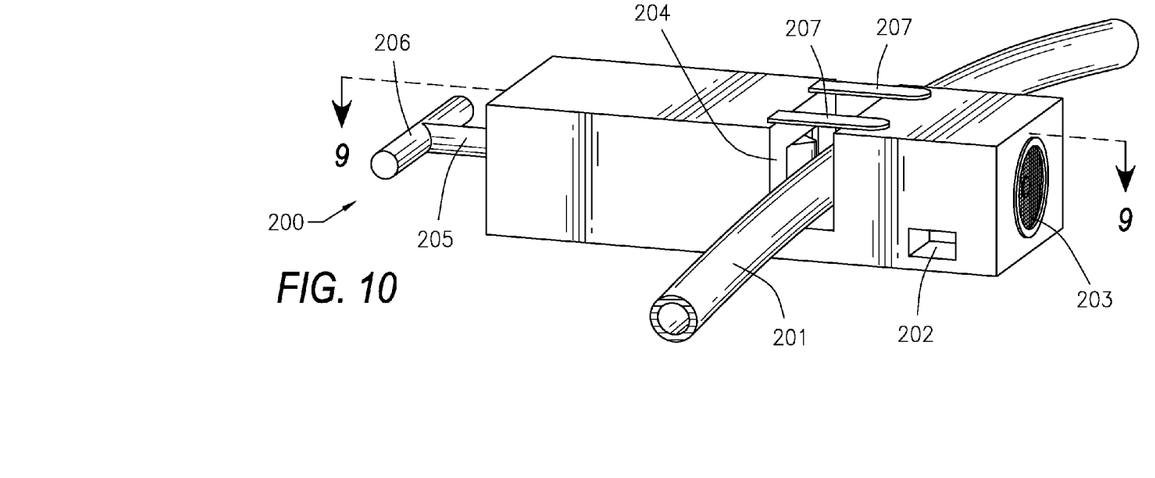
FIG. 10 depicts a perspective view of the early warning and shutdown device.

The multi-conductor cable 52 extending from the patch 40 terminates in a male modular connector 70. The male modular connector 70 will cooperate with a female modular connector 72 connected to multi-conductor cable 52 which, in turn, may be connected to the hemodialysis machine 12 and the component elements previously discussed. Alternately, the multi-conductor cable 52 may connect via connector 202 to an early warning and shutdown device 200, as shown in FIGS. 9 and 10, as discussed below.

Figure 4:
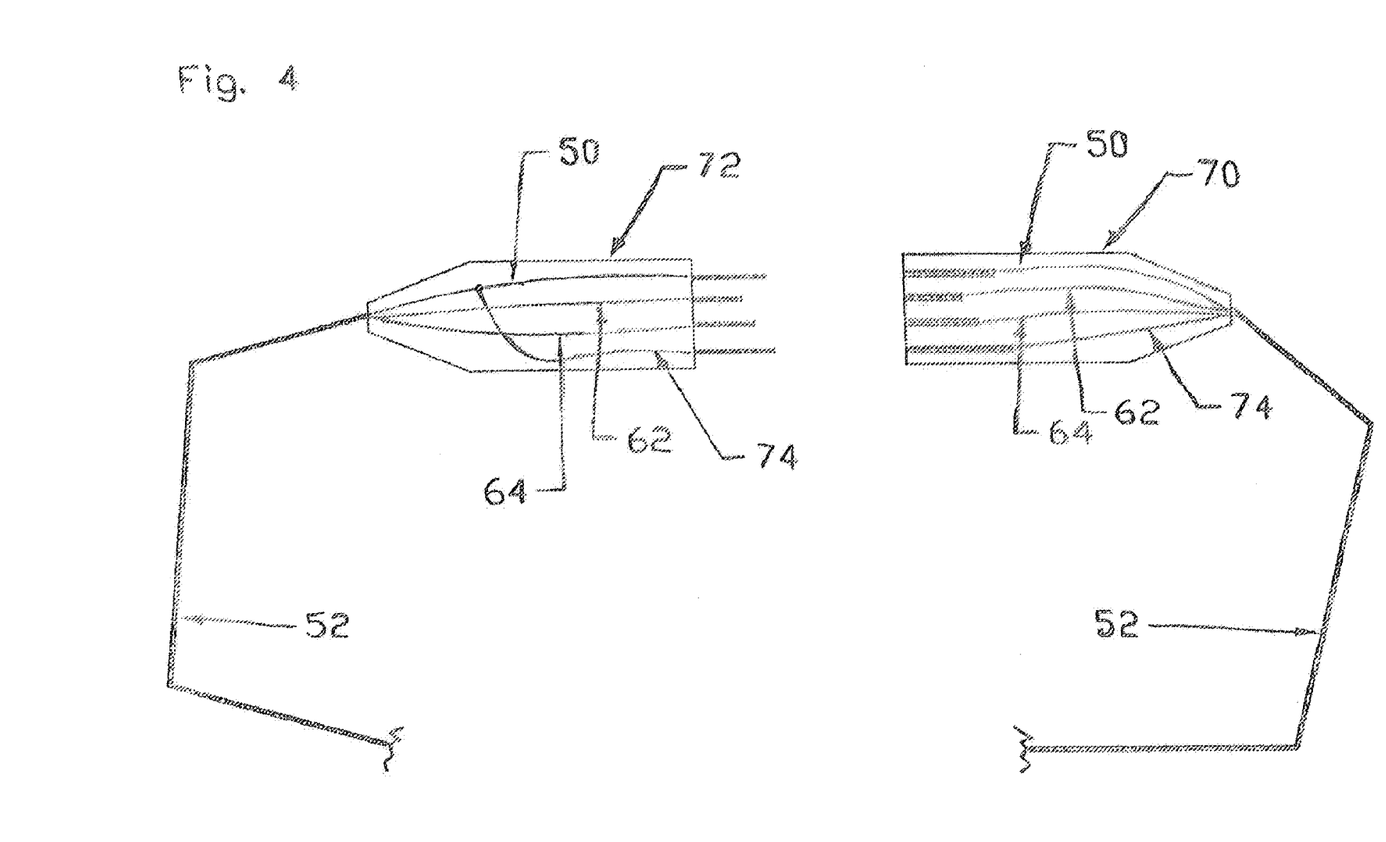
FIG. 4 is a simple illustration of the modular connectors of the detection device.

FIG. 4 illustrates the modular connectors with an optional feature of an optional safety electric loop circuit. In addition to the primary loop circuit 50, the early warning alarm circuit 62 and the emergency shut-down circuit 64, the modular connectors include an optional safety loop circuit 74.

Figure 5:
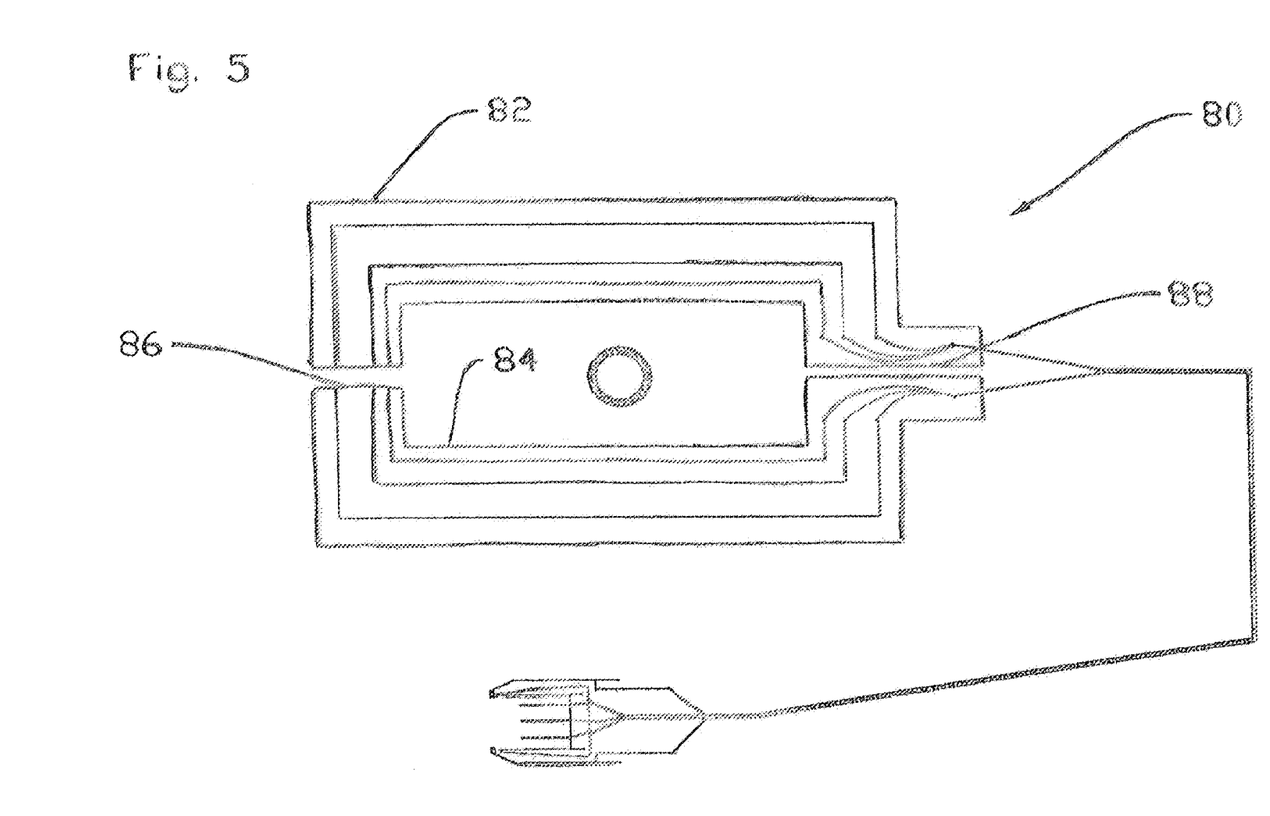
FIG. 5 illustrates a further alternate embodiment of a blood loss detection device (double split design)
Figure 6:
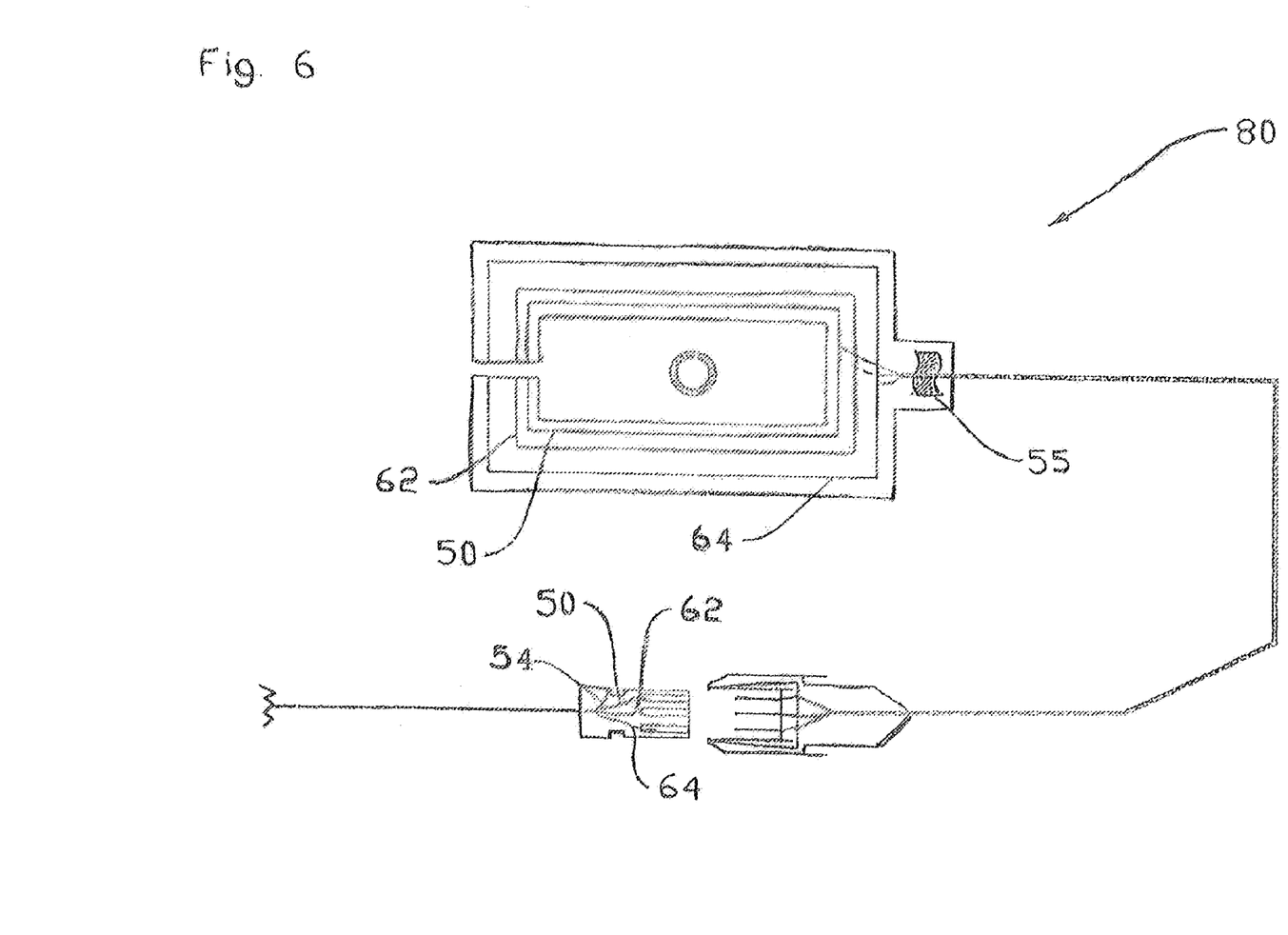
FIG. 6 illustrates a further alternate embodiment of a blood loss detection device with a self-monitoring plug.

FIGS. 5 and 6 show another embodiment of a safety loop modular connector. FIG. 5 shows a further alternate embodiment of the present invention including a patch 80 having a boundary edge 82 and an opening 84. Slits 86 and 88 extend through patch 80 between the boundary edge 82 and the opening 84.

FIG. 5 illustrates a further alternate embodiment 80 of the invention utilizing a double split in the patch and a modular self-monitoring plug.

Figure 7:
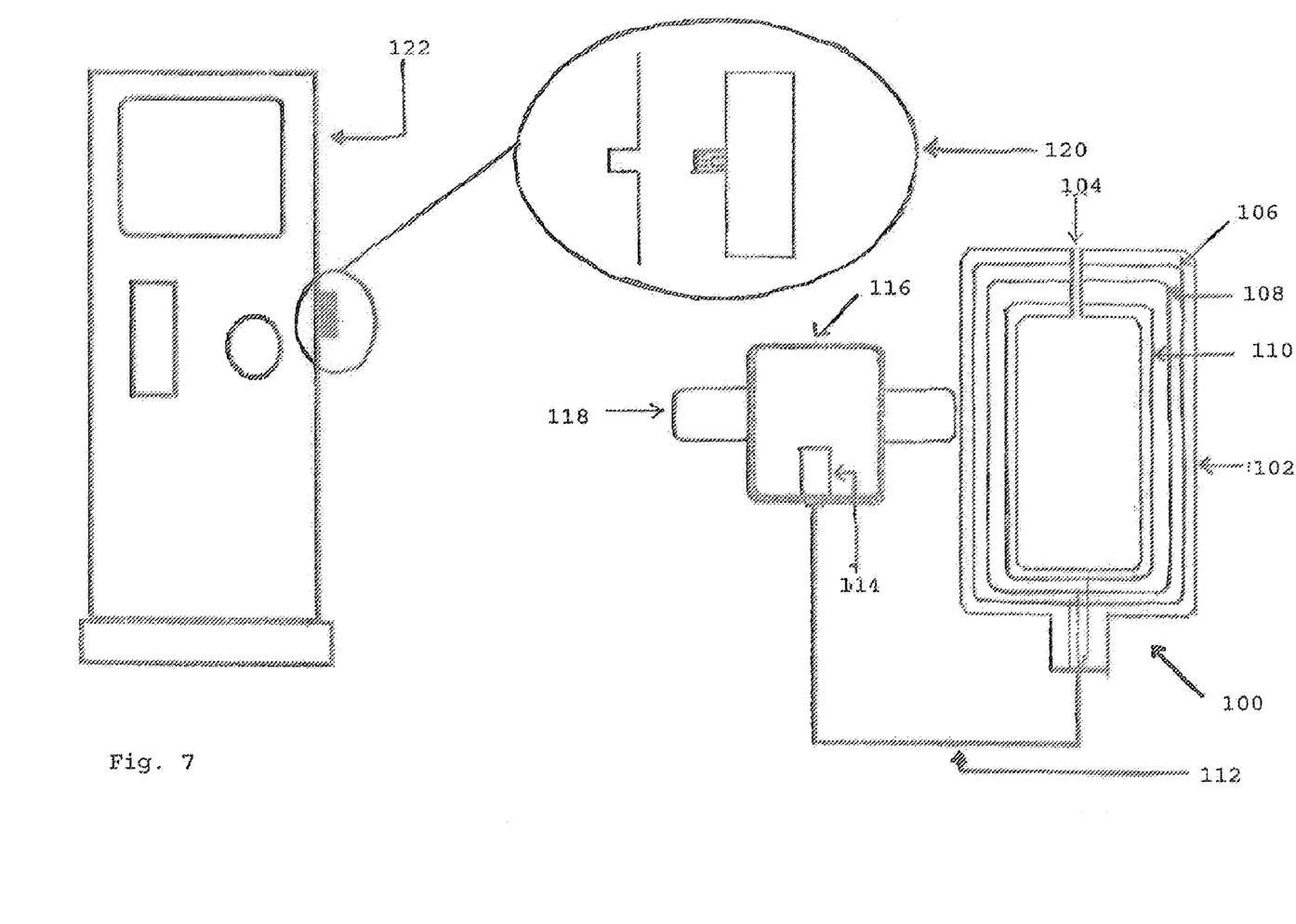
FIG. 7 depicts a simple diagrammatic view of an alternative embodiment of the detection device.
Figure 8:
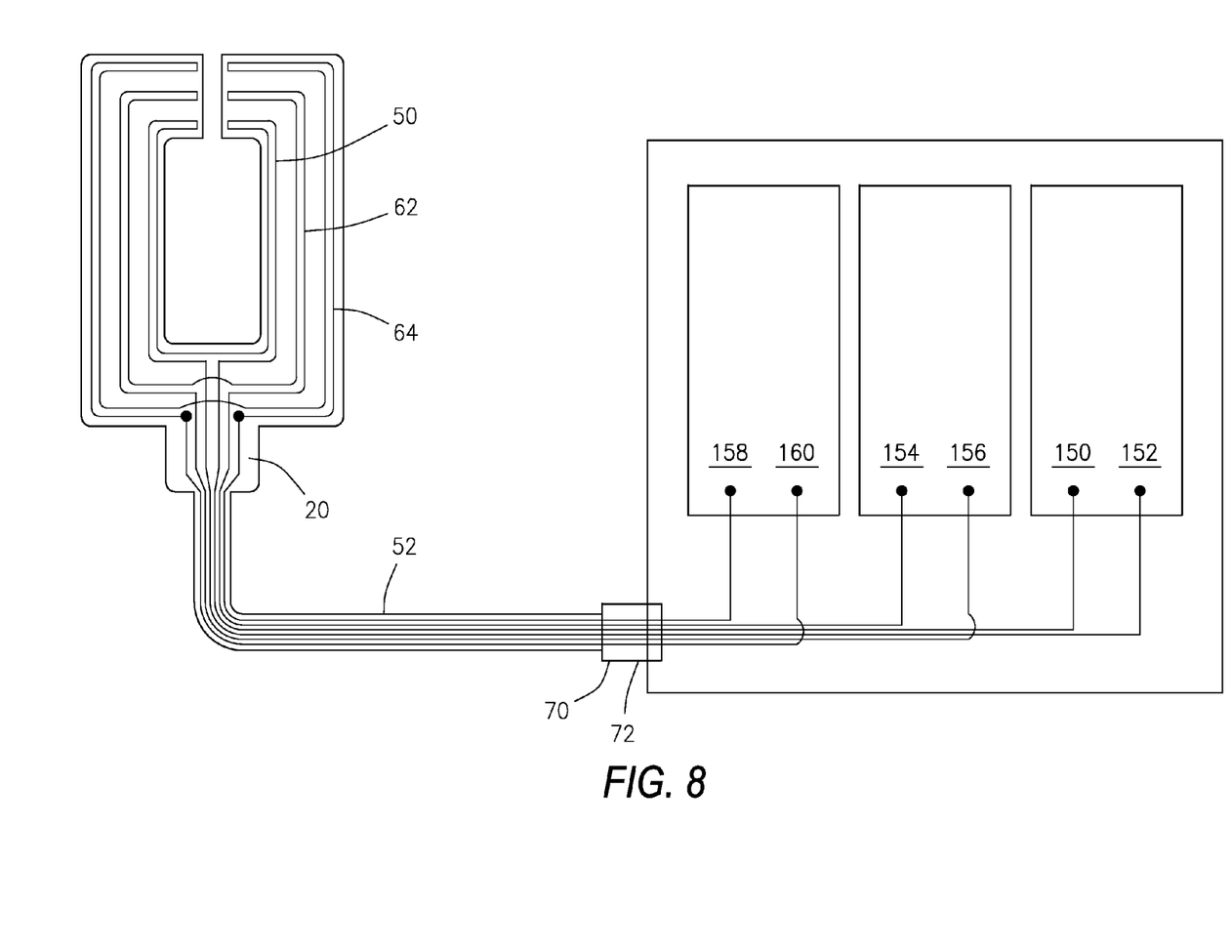
FIG. 8 depicts a simple diagrammatic view of another alternative embodiment of the detection device.

FIG. 7 depicts an alternative embodiment of the present invention. Patch 100 has a boundary edge 102 and a slit 104, as well as a primary loop circuit 106, an early warning alarm loop circuit 108, and an emergency shut-down circuit 110. Primary loop circuit 106, early warning alarm loop circuit 108, and emergency shut-down circuit 110 extend through a multi-conductor cable 112 to a male connector plug 114. Male connector plug 114 is in turn connected to radio transmitter 116. Persons skilled in the art will appreciate that radio transmitter 116 may be any suitable device capable of transmitting a radio signal, preferably a low frequency radio signal.

The radio transmitter 116 features adhesive bands 118 for attachment to a patient's limb. It should be appreciated that any self-adhesive or hook-and-loop adhesive may be utilized, and that radio transmitter 116 need not be attached to the patient's body but could alternatively be attached to a chair, bed rail, instrument cart, instrument stand, night stand, or other nearby furnishing or structure.

Still referring to FIG. 7, a radio receiver 120 is situated within range of radio transmitter 116. Persons skilled in the art will appreciate that radio receiver 120 may be any suitable device that is capable of receiving a radio signal, provided that it is compatible with radio transmitter 116. Radio receiver 120 is operably connected to a downstream device 122. Downstream device 122 may be a medical instrument such as a dialysis machine, or an alarm device capable of activation in response to a radio signal received by radio receiver 120.

The patch 100 and accompanying multi-conductor cable 112 and plug 114 could be disposed of after a single use.

For simple description of operation in FIG. 1, the illustrations will be limited to one input conductor and two return or output circuits or conductor. In the illustration, the inner 24 and outer 22 boundaries enclose three conductors—the primary input conductor circuit loop 50, an emergency notification conductor loop 62 and an emergency shut-down conductor loop 64.

As long as the dialysis machine does not sense a change or input voltage on conductor 62 or 64, the treatment would proceed without interruption. If the machine detects a change in the status of conductor 62, it would activate some type of notification alarm and staff could address the problem and treatment would continue uninterrupted. If at any point during treatment, the machine would detect a change in the status of conductor 64, the machine would initiate an alarm and shut down the blood pump, preventing blood flow to the blood return access site.

The device shown in FIG. 6 also includes a tubing clip 55 to retain the needle and fluid tube (not shown) in association with the patch. The clip may include a sensor circuit that is in a non-alarm state when the tubing is properly secured but if tubing is pulled, opening said clip, same said alarm circuit will be changed to an alarm state notifying patient and medical personnel that tubing is no longer retained by the patch.

A machine connection lead is composed of a multi-conductor cable that originates from control connections within the machine and terminates at a modular female connector. The number of conductors are variable and will depend on the monitoring configuration of the patch/access monitoring device. In the most basic design there would be at least two conductors, the first conductor would provide signal input to the monitoring device/patch and the second would provide a return path to the dialysis machine should a blood loss incident occur. In more advanced designs there would be additional conductors that would communicate other features/embodiments back to the machine for monitoring. In the enclosed details, the machine connection lead would contain four to five conductors. The first conductor 50 would be the signal input conductor or what is referred to as line voltage. The second conductor 62 would be an early warning conductor and would be activated by a small fluid leak. The third conductor 64 would be an emergency shut-down circuit and would only be activated when a larger fluid loss occurs. The fourth conductor 53 and fifth conductor 74 would be utilized in verifying that the modular connectors were properly connected.

As may be appreciated from the foregoing, the present invention may include optional circuits beyond the primary conductor and alarm/shut-down circuits set forth herein.

In an alternate embodiment, the blood loss detection device 10 may not be connected to a dialysis machine, but rather may be connected to a stand-alone early warning and shutdown device 200, as shown in FIGS. 9 and 10. The device 200 may have a modular connector 202 for connecting with the blood loss detection device 10. The device 200 may have an alarm 203 that may be triggered by the detection of fluid by the emergency notification conductor loop 62. The alarm 203 would operate to notify the patient or the patient's care personnel of smaller, less serious fluid loss events. The alarm 203 could be accompanied by a vibration or light emitting system to increase likelihood that a small fluid leak warning is addressed.

The device 200 may also have a channel 204 into which a blood return line 201 may be placed and a clamping mechanism 205 located such that the clamping mechanism 205 may compress the return line 201 when triggered by the detection of fluid by the emergency shut-down conductor loop 64, thus preventing further movement of fluid through the return line 201. The blood return line is typically fabricated from a flexible plastic tubing. In the event of a large fluid loss situation, the clamping mechanism 205 would compress the return line 201 until flow through the tubing is stopped. The clamping mechanism 205 could be activated and operate on many different electro-mechanical, spring loaded, or motor driven principles such as singular or multiple pistons, singular or multiple offset cams, mechanically kinking or twisting of the return line 201, or any number of other ways of arresting the fluid flow.

FIG. 9 shows the clamping mechanism 205 as spring loaded, with a handle 206 for engaging the clamping mechanism 205. When the clamping mechanism is in the open/armed/cocked position, the spring is compressed. The clamping mechanism 205 may also be accompanied by a similar yet unique audible, visual, and/or vibration notification to assure patient and available staff are aware that the fluid flow has been stopped, effectively terminating the treatment.

The channel 204 into which a return line 201 may be placed may have a bracket or strap 207 for securing the return line 201 into position within the channel 204 such that the return line 201 will be compressed when the clamping mechanism 205 is deployed.

The early warning and shutdown device 200 may be small enough to be worn on a patient's arm like a watch or bracelet. Alternately, the device 200 may be made to sit near the patient on a table, chair, or bed.

In operation, the return line 201 is placed within the channel 204 and secured by the bracket or strap 207. The clamping mechanism 205 is placed in an open/armed/cocked position allowing fluid to travel through the return line 201. If the blood loss detection device 10 senses a small fluid loss event, the alarm 203 is sounded. If the blood loss detection device 10 senses a large fluid loss event, a switch will deploy the clamping mechanism 205 to deform the return line 201 until fluid flow is no longer possible, thus terminating the flow of fluids through the return line 201. Alternately, if the blood loss detection device 10 is incapable of distinguishing between a small fluid loss event and a large fluid loss event, the clamping mechanism 205 is deployed upon the first detection of fluid loss.

Ideally, the device 200 would operated at three stages, assuming the blood loss detection device 10 is capable of detecting different stages of fluid loss, as is the blood loss detection device 10 described above. The first stage would be no leak, where everything is functioning normally. The device 200 may incorporate a visual display (not shown) such as a constant or green light. The second stage would be activated when a small fluid leak is detected by closing the normally open circuit between the primary input circuit loop and the early warning circuit loop, this closing of the circuit loop accomplished by a conductive fluid breaching the non-conductive absorbent/semi-permeable barrier between the primary input loop and the early warning loop. The best response to this stage two condition would be an audible alarm 203 with or without a flashing visual indicator and possible an accompanying vibratory alert.

The third and final stage would be the emergency shut down stage and would be initiated when the sensor detects a larger, more severe fluid loss. This more severe fluid loss detection would occur when the normally open circuit between the primary input circuit loop and the emergency shutdown circuit loop becomes closed. The closing of this circuit would be accomplished by a conductive fluid breaching the larger non-conductive absorbent/semi-permeable barrier between the primary input loop and the emergency shut down loop. Since the barrier between the primary input loop and the emergency shut down loop is larger than the barrier between the primary input loop and the early warning loop, a larger fluid loss would be required to initiate this final stage. The response to this stage would be to release or activate the clamping mechanism 205 stopping the fluid flow, possibly accompanied by a louder, more intense audible alert with or without a flashing visual indicator and an intense vibratory alert.

The benefit of the stand-alone early warning and shutdown device 200 is that it may be used with an existing hemodialysis machine without requiring modification to the existing hemodialysis machine. Most hemodialysis machines are programmed to stop pumping if the pressure in the return line becomes too high. Therefore, in operation, when the clamping mechanism 205 is engaged, the increased pressure in the return line 201 will cause the hemodialysis machine to shut down, even though the early warning and shutdown device 200 is not directly connected thereto. Although the device 200 may stand alone, it may also be placed in communication with a dialysis machine, infusion pump, computer, or other notification system via cord and plug or radio frequency.

Figure 11:
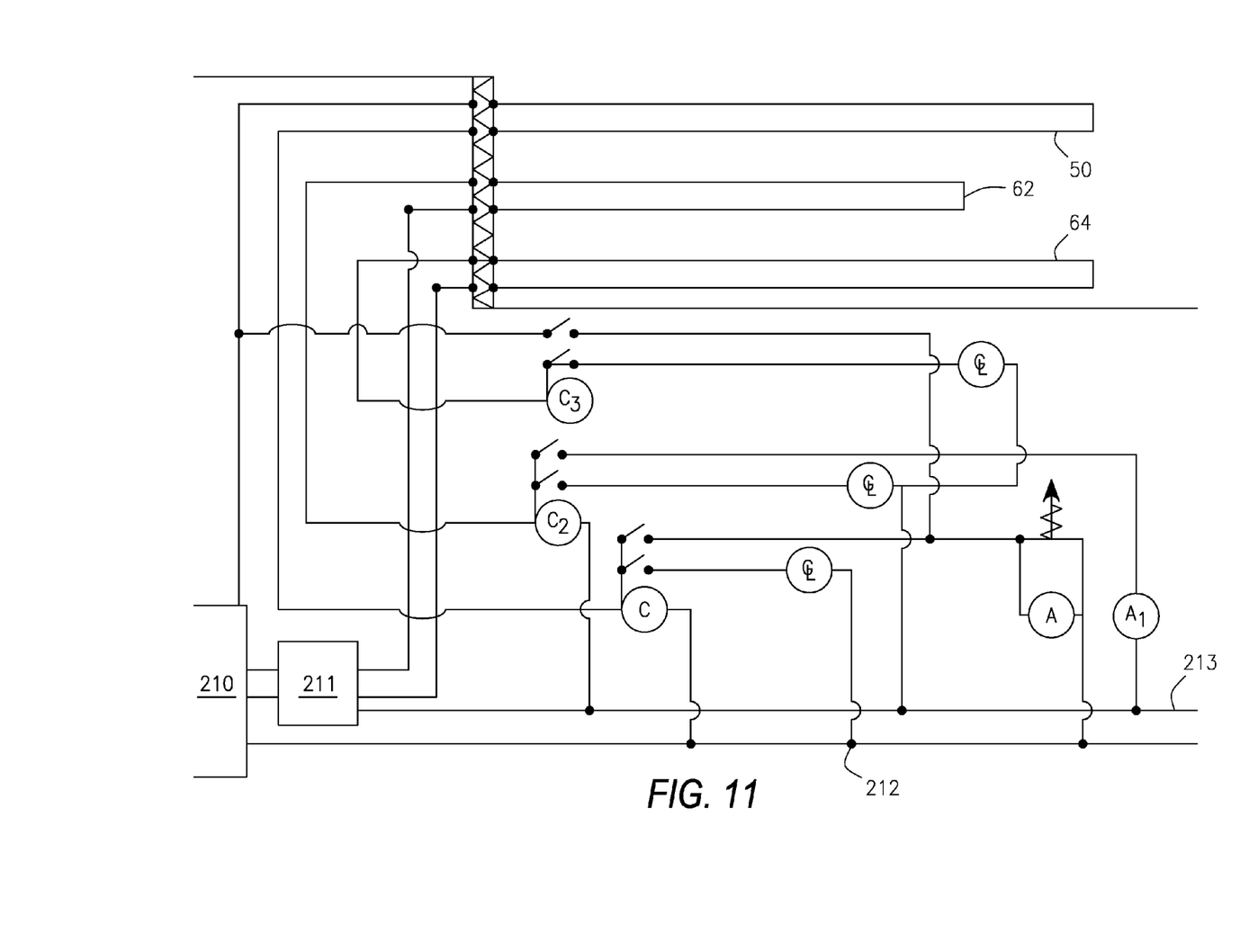
FIG. 11 depicts a circuit diagram for the early warning and shutdown device.

The device 200 may operate on batteries, household power, or both. The device 200 may have a redundant back up power source or may automatically close the clamping mechanism 205 in the event of a power loss. FIG. 11 shows a circuit diagram of the device 200, with power source 210, millivolt transformer 211, 12 v comm 212, millivolt comm 213, primary input circuit 50, early warning circuit 62, and emergency shut down circuit 64.

In addition to the fluid loss detection device 10, other monitoring systems could be integrated into the device 200. One such device could be an air bubble detection system that incorporates a photo sensor on one side of the channel 204 and an LED lamp on the opposite side of the channel 204. The light source would emit light toward the sensor and, if the fluid in the tubing were opaque, such as blood, the light would not be able to reach the photo sensor on the opposite side. However, if a sizeable air bubble were traveling through the tubing, the photo sensor would be able to detect light from the light source and respond with either an alarm, a shutdown, or both an alarm and shutting down/clamping the line 201.

Whereas, the present invention has been described in relation to the drawings attached hereto, it should be understood that other and further modifications, apart from those shown or suggested herein, may be made within the spirit and scope of this invention.

What is claimed is:

1. An early warning and shutdown system for hemodialysis comprising:
    a fluid loss detection device with a central opening surrounding a return access site through which a return line is configured to enter a patient's body, where the fluid loss detection device comprises an emergency shut-down electrical circuit loop surrounding the central opening in a radial plane wherein said emergency shut-down electrical circuit loop is activated by a fluid leak, and an early warning alarm electrical circuit loop surrounded by the emergency shut-down electrical circuit loop in the radial plant, wherein said early warning alarm electrical circuit loop is activated by a smaller fluid leak than the fluid leak that activates the emergency shut-down electrical circuit loop; and
    an automatic shutdown device connected to the fluid loss detection device, the automatic shutdown device comprising:
    a channel capable of receiving the return line; and
    a clamping mechanism located adjacent the channel such that the clamping mechanism does not compress the return line when the clamping mechanism is in an open position but compresses the return line to stop fluids from flowing therethrough when the clamping mechanism is in an engaged position,
    wherein the automatic shutdown device automatically moves the clamping mechanism from the open position to the engaged position when the emergency shut-down electrical circuit loop is activated by a fluid leak.

2. The early warning and shutdown system of claim 1 where the automatic shutdown device further comprises an alarm, wherein the alarm is activated when the early warning alarm electrical circuit loop is activated.

3. The early warning and shutdown system of claim 2 wherein the alarm may produce sounds, lights, vibrations, or any combination thereof.

4. The early warning and shutdown system of claim 1 where the automatic shutdown device further comprises an alarm activated when the emergency shut-down electrical circuit loop is activated.

5. The early warning and shutdown system of claim 4 wherein the alarm may produce sounds, lights, vibrations, or any combination thereof.

6. The early warning and shutdown system of claim 1 where the fluid loss detection device connects to the automatic shutdown device via a modular connector.

7. The early warning and shutdown system of claim 1 where the clamping mechanism is actuated by spring, electrical, mechanical, pneumatic, electromechanical or electropneumatic force.

8. The early warning and shutdown system of claim 1 where the automatic shutdown device further comprises a bracket or strap capable of securing the return line within the channel.

9. The early warning and shutdown system of claim 1 where the automatic shutdown device attaches to the patient's arm.

* * * * *